United States Patent [19]

Gyory et al.

[11] Patent Number: 5,582,587
[45] Date of Patent: *Dec. 10, 1996

[54] IONTOPHORETIC DELIVERY DEVICE AND METHOD OF HYDRATING SAME

[75] Inventors: J. Richard Gyory, San Jose; John R. Peery, Stanford, both of Calif.

[73] Assignee: Alza Corporation, Palo Alto, Calif.

[ * ] Notice: The term of this patent shall not extend beyond the expiration date of Pat. No. 5,310,404.

[21] Appl. No.: 239,500

[22] Filed: May 9, 1994

Related U.S. Application Data

[63] Continuation of Ser. No. 892,554, Jun. 1, 1992, Pat. No. 5,310,404.

[51] Int. Cl.[6] .................................................. A61N 1/30
[52] U.S. Cl. ............................................ 604/20; 607/153
[58] Field of Search ....................... 604/20; 607/149–153

[56] References Cited

U.S. PATENT DOCUMENTS

| | | | |
|---|---|---|---|
| 3,991,755 | 11/1976 | Vernon et al. | |
| 4,141,359 | 2/1979 | Jacobsen et al. | |
| 4,250,878 | 2/1981 | Jacobsen et al. | |
| 4,383,529 | 5/1983 | Webster | 604/20 |
| 4,398,545 | 8/1983 | Wilson | |
| 4,416,274 | 11/1983 | Jacobsen et al. | 128/803 |
| 4,474,570 | 10/1984 | Ariura et al. | 604/20 |
| 4,731,049 | 3/1988 | Parsi | 604/20 |
| 4,764,164 | 8/1988 | Sasaki | 604/20 |
| 4,842,577 | 6/1989 | Konno et al. | 604/20 |
| 4,968,297 | 11/1990 | Jacobsen et al. | 604/20 |
| 5,053,001 | 10/1991 | Reller et al. | 604/20 |
| 5,084,006 | 1/1992 | Lew et al. | 604/20 |
| 5,087,241 | 2/1992 | Mathiesen et al. | 604/20 |
| 5,087,242 | 2/1992 | Petelenz et al. | 604/20 |
| 5,156,591 | 10/1992 | Gross et al. | 604/20 |
| 5,158,537 | 10/1992 | Haak et al. | 604/20 |
| 5,160,316 | 11/1992 | Henley | 604/20 |
| 5,310,404 | 5/1994 | Gyory et al. | 604/20 |

FOREIGN PATENT DOCUMENTS

| | | |
|---|---|---|
| 410009 | 10/1933 | United Kingdom . |
| 9207619 | 5/1992 | WIPO . |
| 9207618 | 5/1992 | WIPO . |
| 9210235 | 6/1992 | WIPO ...................................... 604/20 |

Primary Examiner—John D. Yasko
Assistant Examiner—Ronald K. Stright, Jr.
Attorney, Agent, or Firm—D. Byron Miller; Felissa H. Cagan; Steven F. Stone

[57] ABSTRACT

A dry-state iontophoretic drug delivery device (10, 30) is provided. The device has drug and electrolyte reservoirs (15, 16) which are initially in a non-hydrated condition. In one embodiment of the invention, a sealed liquid-containing pouch (21, 22) is provided in each electrode assembly (8, 9). Water or other liquid (20) is released from the pouch (21, 22) by pulling a tab (27, 28) attached to a portion (25, 26) of the pouch (21, 22) which is capable of being torn or ripped in order to hydrate the drug and electrolyte reservoirs (15, 16) and activate the device (10, 30). In another embodiment, the device (30) is held in a package (32). The device (30) has pouches (21, 22) which release their liquid contents automatically upon removal of the device (30) from the package (32). In yet another embodiment, the device (40) is held in a package (42) having a compression zone (46). The pouches (21, 22) must be moved through the compression zone (46) when removing the device (40) from the package (42). Compression causes the pouches (21, 22) to rupture and release the hydrating liquid (20).

11 Claims, 7 Drawing Sheets

IONTOPHORETIC DELIVERY DEVICE AND METHOD OF HYDRATING SAME

This is a continuation of U.S. patent application Ser. No. 07/892,554 filed Jun. 1, 1992, now U.S. Pat. No. 5,310,404.

TECHNICAL FIELD

This invention relates to a device for delivering an agent transdermally or transmucosally by iontophoresis. More particularly, this invention relates to an electrically powered iontophoretic delivery device having electrodes which can be hydrated or otherwise activated by the addition of liquid just before applying the device to the body.

BACKGROUND ART

Iontophoresis has in the past been defined as "the introduction, by means of electric current, of ions of soluble salts into the tissues of the body for therapeutic purposes." Iontophoretic devices for delivering ionized drugs through the skin have been known since the early 1900's. Deutsch UK Patent No. 410,009 (1934) describes an iontophoretic device which overcame one of the disadvantages of such early devices, namely that the patient needed to be immobilized near the source of electric current. The Deutsch device was powered by a galvanic cell formed from the electrodes and the material containing the drug to be delivered transdermally. The galvanic cell produced the current necessary for iontophoretically delivering the drug. This device thus allowed the patient to move around during iontophoretic drug delivery and thus imposed substantially less interference with the patient's daily activities.

Today, iontophoresis is not limited solely to the delivery of ions (e.g., drug ions) into the body by means of electric current. For example, it is now recognized that iontophoretic delivery devices can be used to deliver an uncharged drug or agent into the body. This is accomplished by a process called electroosmosis. Electroosmosis is the transdermal flux of a liquid solvent (e.g., the liquid solvent containing the uncharged drug or agent) which is induced by the presence of an electric field imposed across the skin by the donor electroae. As used herein, the terms "iontophoresis" and "iontophoretic" refer to (1) the delivery of charged drugs or agents by electromigration, (2) the delivery of uncharged drugs or agents by the process of electroosmosis, (3) the delivery of charged drugs or agents by the combined processes of electromigration and electroosmosis, and/or (4) the delivery of a mixture of charged and uncharged drugs or agents by the combined processes of electromigration and electroosmosis.

Recently, a number of United States patents have issued in the iontophoresis field, indicating a renewed interest in this mode of drug delivery. For example, Vernon et al U.S. Pat. No. 3,991,755; Jacobsen et al U.S. Pat. No. 4,141,359; Wilson U.S. Pat. No. 4,398,545; and Jacobsen U.S. Pat. No. 4,250,878 disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate, insulin and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

In presently known iontophoretic devices, at least two electrodes are used. Both of these electrodes are disposed so as to be in intimate electrical contact with some portion of the skin or other membrane surface of the body. One electrode, called the active or donor electrode, is the electrode from which the ionic substance, medicament, drug precursor or drug is delivered into the body by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged (ie, a cation), then the anode will be the active electrode and the cathode will serve to complete the circuit. If the ionic substance to be delivered is negatively charged (ie, an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

Iontophoretic delivery devices generally require a reservoir or source of the beneficial agent to be iontophoretically delivered or introduced into the body. Examples of such reservoirs or sources of agents include a pouch or cavity as described in the previously mentioned Jacobsen U.S. Pat. No. 4,250,878, a porous sponge or pad as disclosed in Jacobsen et al U.S. Pat. No. 4,141,359, or a pre-formed gel body as described in Webster U.S. Pat. No. 4,383,529 and Ariura et al U.S. Pat. No. 4,474,570. Such drug reservoirs are electrically connected to the anode or the cathode of an iontophoresis device to provide a fixed or renewable source of one or more desired agents.

Iontophoretic delivery devices which are attachable at a skin surface and rely on electrolyte fluids to establish electrical contact with such skin surfaces can be divided into at least two categories. The first category includes those devices which are prepackaged with the liquid electrolyte contained in the electrode receptacle. The second type of device uses dry-state electrodes whose receptacles are customarily filled with a drug/electrolyte solution immediately prior to application to the body. With both types of devices, the user currently experiences numerous problems which make their use both inconvenient and problematic.

With respect to the prefilled device, storage is a major concern. Many drugs have poor stability when in solution. Accordingly, the shelf life of prefilled iontophoretic drug delivery devices is unacceptably short. Corrosion of the electrodes and other electrical components is also a potential problem with prefilled devices. For example, the return electrode assembly usually contains an electrolyte salt such as sodium chloride which over time can cause corrosion of metallic and other electrically conductive materials. Another problem with prefilled electrodes concerns maintaining the sterility of the electrodes and preventing microbial growth therein. This is a particular problem when the liquid used to conduct iontophoresis is water. Although antimicrobial agents can be added to the drug and/or electrolyte reservoirs of an iontophoretic delivery device, the addition of such agents tends to compromise the efficiency of agent delivery. Leakage is another serious problem with prefilled iontophoretic drug delivery devices. Leakage of drug or electrolyte from the electrode receptacle can result in an inoperative or defective state. Furthermore, such prefilled devices are difficult to apply because the protective seal which covers the electrode opening and retains the fluid within the receptacle cavity must be removed prior to application on the skin. After removal of this protective seal, spillage often occurs in attempting to place the electrode on the skin. Such spillage impairs the desired adhesive contact of the electrode to the skin and also voids a portion of the receptacle cavity. The consequent loss of drug or electrolyte solution can disrupt electrical contact with the electrode and otherwise disrupts the desired uniform potential gradient applied by these devices.

Although dry-state electrodes have numerous advantages in ease of storage, several problems remain. For example, the drug and electrolyte receptacles of such a device are conventionally filled through an opening prior to application of the device to the patient's skin. Therefore, the same problem of spillage and loss of drug or electrolyte upon application occurs as with the prefilled electrode.

Frequently, such electrodes are not well structured to develop the proper uniform current flow required in iontophoresis applications. Such nonuniform current flow may result from the occurrence of air pockets within the receptacle cavity at the skin surface. Such effects are particularly troublesome in iontophoresis applications, where a nonuniform current distribution may result in excessive skin irritation or "burning".

More recently, iontophoretic delivery devices have been developed in which the donor and counter electrode assemblies have a "multilaminate" construction. In these devices, the donor and counter electrode assemblies are each formed of multiple layers of (usually) polymeric matrices. For example, Parsi U.S. Pat. No. 4,731,049 discloses a donor electrode assembly having hydrophilic polymer based electrolyte reservoir and drug reservoir layers, a skin-contacting hydrogel layer, and optionally one or more semipermeable membrane layers. In addition, Ariura et al U.S. Pat. No. 4,474,570 discloses a device wherein the electrode assemblies include a conductive resin film electrode layer, a hydrophilic gel reservoir layer, an aluminum foil conductor layer and an insulating backing layer.

The drug and electrolyte reservoir layers of iontophoretic delivery devices have typically been formed of hydrophilic polymers. See for example, Ariura et al, U.S. Pat. No. 4,474,570; Webster U.S. Pat. No. 4,383,529 and Sasaki U.S. Pat. No. 4,764,164. There are several reasons for using hydrophilic polymers. First, water is biocompatible, highly polar and therefore a preferred solvent for many drugs. Secondly, hydrophilic polymer components (ie, the drug reservoir in the donor electrode and the electrolyte reservoir in the counter electrode) can be hydrated while attached to the body by absorbing water from the skin or from a mucosal membrane. For example, skin contacting electrodes can be hydrated by absorbing sweat or water from transepidermal water loss. Similarly, electrodes attached to an oral mucosal membrane can be hydrated by absorbing saliva. Once a sufficient quantity of water is absorbed into the drug and electrolyte reservoirs, ions are able to move through the reservoirs and across the tissue, enabling the device to deliver agent to the body. Hydrogels have been particularly favored for use as the drug reservoir matrix and electrolyte reservoir matrix in iontophoretic delivery devices, in part due to their high equilibrium water content and their ability to absorb water from the body. In addition, hydrogels tend to have good biocompatibility with the skin and with mucosal membranes. However, since many drugs and certain electrode components are unstable in the presence of water, iontophoretic drug delivery devices having a drug reservoir formed of a prehydrated hydrogel may also have an unacceptably short shelf life. One solution to the drug stability problem is to use hydrophilic polymer drug and electrolyte reservoirs which are in a substantially dry state, ie, in a non-hydrated condition. The drug and/or electrolyte can for example be dry blended with the hydrophilic polymer and then cast or extruded to form a non-hydrated, though hydratable, drug or electrolyte containing reservoir. Unfortunately, the non-hydrated hydrophilic polymer components must first absorb sufficient quantities of water from the body before the device can operate to deliver drug. This delivery start-up period can take in excess of several hours. This delay makes many devices unsuited for their intended purpose. For example, when using an iontophoretic delivery device to apply a local anesthetic in preparation for a minor surgery (e.g., surgical removal of a mole), the surgeon and the patient must wait until the drug and electrolyte reservoirs of the delivery device become sufficiently hydrated before the anesthetic is delivered in sufficient quantities to induce anesthesia. Similar delays are encountered with other drugs.

In response to the difficulty of iontophoretic delivery of a drug which is unstable in water, Konno et al in U.S. Pat. No. 4,842,577 discloses in FIG. 4 an iontophoretic electrode assembly having a substantially non-hydrated drug containing matrix and a separate water reservoir which is initially sealed, using a foil sheet, from the drug containing portions of the electrode. In order to activate the Konno et al electrode assembly, the top of the water reservoir container is depressed, causing the foil sheet to break and thereby release the water into the non-hydrated drug-containing matrix. Unfortunately, this electrode design is not only difficult to manufacture but also is subject to severe handling restrictions. In particular, there is a tendency for the foil seal to be inadvertently broken during manufacture, packaging and handling of the electrode. This can have particularly drastic consequences especially when the seal is broken during manufacture or shipping of the device. Once the seal is broken, water is wicked into the drug-containing reservoir which can cause degradation of the drug and/or other components before the device is ever used.

Another disaavantage of using non-hydrated hydrophilic polymer components is that they have a tendency to delaminate from other parts of the electrode assembly during hydration. For example, when utilizing a drug reservoir matrix or an electrolyte reservoir matrix composed of a hydrophilic polymer, the matrix begins to swell as it absorbs water from the skin. In the case of hydrogels, the swelling is quite pronounced. Typically, the drug or electrolyte reservoir is in either direct contact, or contact through a thin layer of an ionically conductive adhesive, with an electrode. Typically, the electrode is composed of metal (e.g., a metal foil or a thin layer of metal deposited on a backing layer) or a hydrophobic polymer containing a conductive filler (e.g., a hydrophobic polymer loaded with carbon fibers and/or metal particles). Unlike the hydrophilic drug and electrolyte reservoirs, the electrodes do not absorb water and do not swell. The different swelling properties of the hydrophilic reservoir and the electrode, or the ionically conductive adhesive, results in shearing along their contact surfaces. In severe cases, the shearing can result in the complete loss of electrical contact between the electrode and the drug/electrolyte reservoir resulting in an inoperable device.

DISCLOSURE OF THE INVENTION

Thus, it is an object of the present invention to provide an iontophoretic drug delivery device with electrode assemblies which are manufactured in an initially non-hydrated or dry state but which can be quickly hydrated prior to placement on the body.

It is another object of this invention to provide an improved method of quickly hydrating the electrode assemblies in an iontophoretic delivery device in order to minimize the "start-up" delay of an iontophoretic delivery device.

It is a further object of this invention to provide an iontophoretic drug delivery device which cannot be inadvertently hydrated prior to actual use.

It is still another object of this invention to provide an iontophoretic agent delivery device, and an "automatic" method of hydrating same, which method requires no extra effort or intervention on the part of the user other than removing the device from its package.

These and other objects are met by an electrically powered iontophoretic agent delivery device and a method of hydrating same. The delivery device includes at least one dry state electrode assembly and a source of electrical power which is electrically connected to the electrode assembly. The electrode assembly includes an agent reservoir comprised of a substantially non-hydrated hydratable matrix adapted to contain the agent to be delivered. The electrode assembly is adapted to be placed in agent transmitting relation with a body surface, such as intact skin or a mucosal membrane, for electrically assisted delivery of agent therethrough. The electrode assembly also includes an electrode in electrical contact with both the power source and the agent reservoir. The electrode assembly has a container which contains a liquid for hydrating the substantially non-hydrated agent reservoir matrix. At least a portion of the container wall is comprised of a liquid impermeable material which is broken in order to release the liquid.

In accordance with one embodiment of the invention, the liquid impermeable material is capable of being ripped or torn. A pull tab is provided having one portion attached to the liquid impermeable material and another portion extending out from the electrode assembly. Pulling the tab relative to the liquid impermeable material causes the material to rip or tear, thereby releasing the liquid from the container. The electrode assembly also has liquid flow control means for directing the flow of liquid released from the container to the substantially non-hydrated matrix. The electrode assembly is activated (ie, hydrated) by pulling the tab which causes the liquid impermeable material to rip or tear, thereby releasing the liquid from the container. The released liquid then flows into the non-hydrated matrix.

Preferably, the tab is attached to a package in which the device is held. The tab is pulled relative to the liquid impermeable material when the electrode assembly is removed from the package. Thus, the action of removing the electrode assembly from the package "automatically" hydrates and activates the electrode assembly. Alternatively, the tab is attached to a release liner covering a skin contacting surface of the electrode assembly. The tab is pulled relative to the liquid impermeable material when the release liner is removed from the electrode assembly. Thus, the action of removing the release liner "automatically" hydrates and activates the electrode assembly.

In accordance with another embodiment of the invention, the liquid impermeable material ruptures when the pressure within the is sealed container reaches a predetermined level. The device is held within a package having a compression zone therein. When the device is removed from the package, the sealed container is forced through the compression zone causing the pressure within the sealed container to rise above the predetermined level thereby causing the liquid impermeable material to rupture and release the hydrating liquid.

In another embodiment, the dry state electrode assembly is provided with a sealed flexible pouch containing both a hydrating liquid and a punch. The punch has a blade which, when activated, punctures the pouch and provides a liquid flow path from the pouch to the non-hydrated agent reservoir matrix. The blade is activated by compressing the flexible pouch. Means are provided for preventing accidental activation of the blade by pressure inadvertently applied to the pouch.

In yet another embodiment, the dry state electrode assembly is provided with a sealed container containing a hydrating liquid. A punch is positioned between the container and a non-hydrated reservoir. The punch has at least one blade which, when activated, punctures the wall of the container and thereby releases the liquid from the sealed container. The punch has an opened structure which permits the release liquid to flow through the punch and into the hydratable reservoir.

BRIEF DESCRIPTION OF THE DRAWINGS

In the figures, like elements are designated by the same reference number in the several drawings.

MODES FOR CARRYING OUT THE INVENTION

Figure 1:
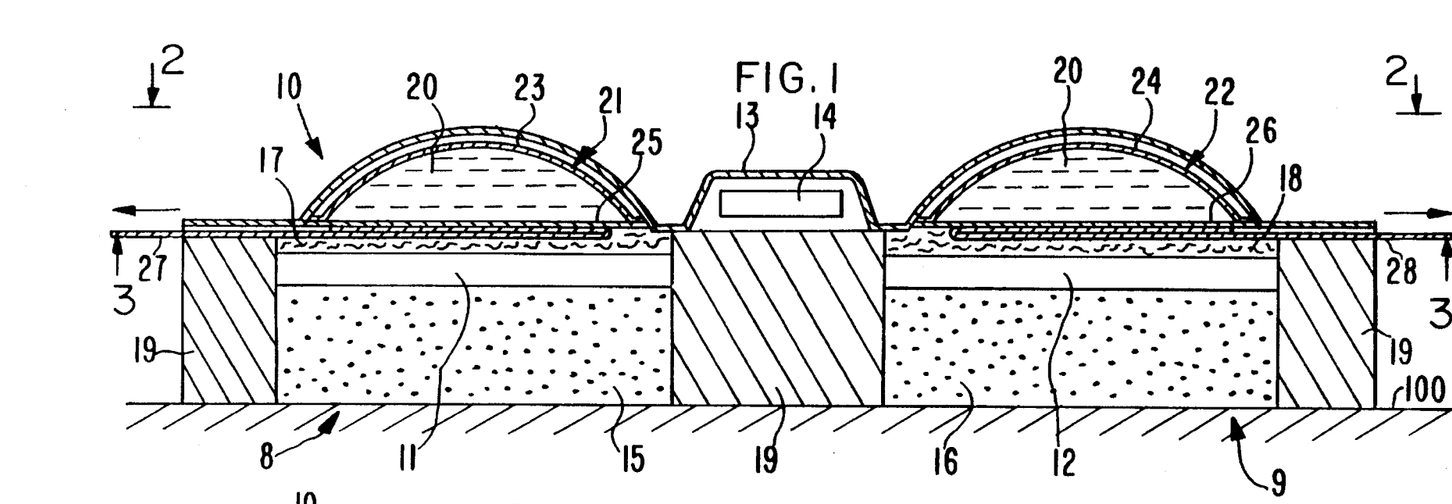
FIG. 1 is a sectional side view of an iontophoretic drug delivery device according to the present invention.

FIG. 1 is a side sectional view of an iontophoretic delivery device 10 for delivering a beneficial agent through a body surface 100 such as intact skin or a mucosal membrane. Iontophoretic delivery device 10 includes a donor electrode assembly 8 and a counter electrode assembly 9. The donor electrode assembly 8 and the counter electrode assembly 9 are separated by insulator 19. Insulator 19 prevents the electrode assemblies 8 and 9 from short circuiting the body by preventing direct electrical and/or ion transport between the electrode assemblies 8 and 9 (ie, without current in the form of ions passing through the body). Insulator 19 can optionally be provided around the outer peripheries of electrode assemblies 8 and 9 (as shown in FIG. 1) to prevent contamination of is reservoirs 15 and 16 by fluids such as bath water while the device 10 is positioned on body surface 100 (e.g., the skin). Insulator 19 is preferably formed of a hydrophobic non-conducting polymeric material which is impermeable to both the passage of ions and water. Preferred insulating materials include nonporous ethylene vinyl acetate, polyisoprenes, polypropylenes, copolymers of isoprene and propylene and in general any closed cell foamed plastic.

Electrode assemblies 8 and 9 are connected in series, using well known electrical conductors such as metal foils, wires, printed circuits or electrically conductive films (not shown), with an electrical power source. The power source and the electrical conductors are schematically shown as member 14. The power source used to power device 10 is typically one or more low voltage (e.g., 1 to 3 volt button cells) batteries. A flexible and water impermeable housing 13 covers the top of device 10 including member 14 with its associated electrical components.

The donor electrode assembly 8 includes an electrode 11 and a reservoir 15. The reservoir 15 contains the beneficial agent to be iontophoretically delivered by device 10. A rate controlling membrane layer (not shown) may optionally be positioned between the reservoir 15 and the body surface 100 for controlling the rate at which the agent is delivered to the body surface 100 or for limiting the delivery of agent to the body surface 100 when the device is turned off. Counter electrode assembly 9 contacts the body surface 100 at a location spaced apart from electrode assembly 8. Counter electrode assembly 9 includes an electrode 12 and a reservoir 16. Reservoir 16 contains an electrolyte, e.g., a water soluble electrolyte salt.

Device 10 can be adhered to the body surface 100 by means of any known means for applying an iontophoretic delivery device to a body surface. For example, device 10 may be adhered to body surface 100 by ion-conducting adhesive layers applied to the body-facing surfaces of reservoirs 15 and 16. Alternatively, device 10 may be adhered to the body surface 100 using an adhesive overlay. Any of She conventional adhesive overlays used to secure passive transdermal delivery devices to the skin may be used. Still further, device 10 may be adhered to body surface 100 through the use of tacky reservoir matrix materials for reservoirs 15 and 16 or through the use of a tacky insulator 19. Still further, device 10 may be secured in ion-transmitting relation to body surface 100 by a strap or an elastic band, e.g., a strap or band encircling a body part such as an arm or a leg.

When the device 10 is in storage, no current flows because the device does not form a closed circuit. When the device 10 is placed on the skin or mucosal membrane of a patient and the electrode assemblies 8 and 9 are sufficiently hydrated to allow ions to flow through the various layers of electrode assemblies 8 and 9, the circuit between the electrodes is closed and the power source begins to deliver current through the device and through the body of the patient. The donor and counter electrode assemblies 8 and 9 normally include a strippable release liner, not shown, which is removed prior to application of electrode assemblies 8 and 9 to body surface 100.

The donor electrode assembly 8 includes an optional layer 17 of a liquid-wicking material positioned between electrode 11 and a sealed liquid-containing container or pouch 21. The wall 23 of pouch 21 is formed of a liquid-impermeable material, preferably a flexible sheet material such as nigh density polyethylene, polypropylene or a metal foil such as aluminum foil. Pouch 21 is sealed along the side adjacent wicking layer 17 with a liquid-impermeable material 25 which is shown in the form of a sheet. Sheet 25 is broken, as described hereinafter, in order to release liquid 20 from pouch 21.

Like donor electrode assembly 8, the counter electrode assembly also has a sealed container or pouch 22 containing a liquid 20. An optional liquid wicking layer 18 is provided between electrode 12 pouch 22. Like pouch 21, the wall 24 of pouch 22 is also formed of a liquid impermeable material, and preferably a flexible sheet material such as high density polyethylene, polypropylene or a metal foil such as aluminum foil. The liquid 20 contained in pouches 21 and 22 is typically water, although other liquids including non-aqueous liquids, can also be used. Pouch 22 is sealed along the side adjacent wicking layer 18 with a liquid-impermeable material 26 which is shown in the form of a sheet. Like sheet 25, sheet 26 can also be broken.

Figure 2:
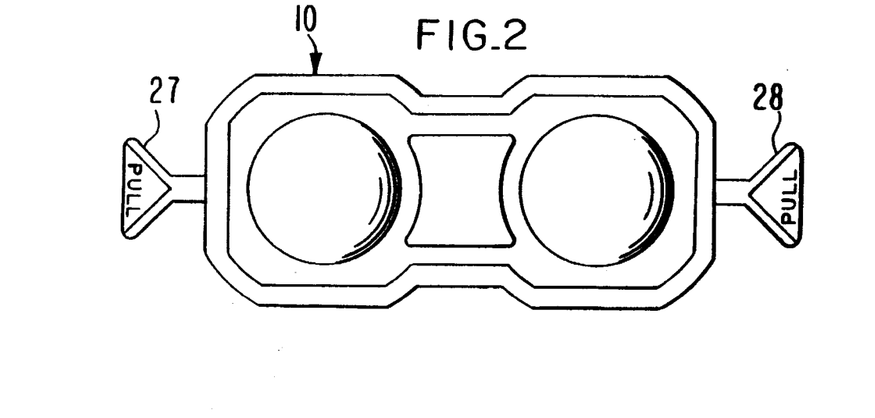
FIG. 2 is a top view of the device shown in FIG. 1.
Figure 3:
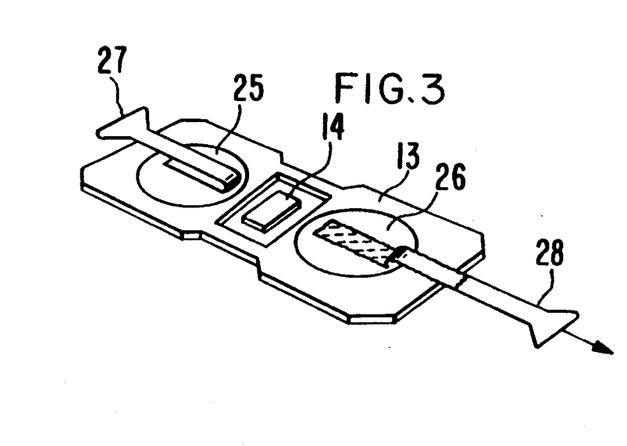
FIG. 3 is a bottom view of the device shown in FIG. 1, taken along line 3—3 in FIG. 1.
Figure 4:
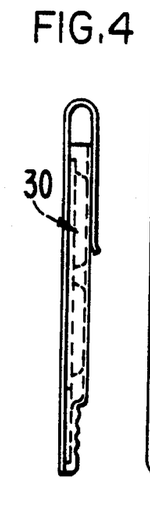
FIG. 4 is a side view of a package for holding an iontophoretic delivery device according to one embodiment of the present invention.

In the embodiment illustrated in FIG. 1, sheets 25 and 26 are capable of being ripped or torn and preferably have a tear strength in the range of about 0.2 to 2.3 kg. Most preferably sheets 25 and 26 are comprised of a thin, water impermeable film or foil such as polymer films, metal foils, metalized polymer films such as metal deposited on a polymer film and metal foil/polymer film laminates. As best shown in FIGS. 1 and 3, a pull tab 27 is attached to sheet 25. Similarly, a pull tab 28 is attached to sheet 26. Each of the pull tabs 27 and 28 is folded over on itself and has a graspable end portion which extends beyond the periphery of device 10 as best shown in FIG. 2. Pull tabs 27 and 28 are attached to sheets 25 and 26, respectively, in a manner having greater strength than the tear strength of the material of sheets 25 and 26 so that upon pulling, or otherwise placing tensile stress on pull tabs 27 and 28, the material of sheets 25 and 26 will fail and rip or tear along the region where tabs 27 and 28 are attached to sheets 25 and 26. If necessary, sheets 25 and 26 may be intentionally weakened in the regions where pull tabs 27 and 28 are attached to sheets 25 and 26, respectively, in order to ensure proper tearing of sheets 25 and 26.

The pull tabs 27 and 28 provide an important advantage not found in prior art hydratable devices. With devices such as those disclosed in Konno et al U.S. Pat. No. 4,842,577, there was a tendency for the seal between the water reservoir and the non-hydrated portions of the electrode to be inadvertently broken due to accidental forces exerted on the water reservoir during manufacture, packaging and/or handling of the electrode. With the present design, this problem has been eliminated since liquid 20 is only released by the action of grasping and pulling tabs 27 and 28. The action of pulling tabs 27 and 28 requires an intentional action on the part of the user to activate (ie, hydrate) device 10. It is much less likely that device 10 will be inadvertently activated, in comparison with devices which are activated by applying pressure on the exterior of the device in order to break a seal within the device. Thus, the pulling required with tabs 27 and 28 helps to prevent inadvertent hydration of the underlying electrode assembly caused by pressure inadvertently applied to device 10. Thus, the present design provides an important improvement over that disclosed by Konno et al.

In order to activate delivery device 10, reservoirs 15 and 16 (as well as any optional ion-conducting membrane and/or adhesive layers within electrode assemblies 8 and 9) must become sufficiently hydrated to enable agent to be transported therethrough by iontophoresis. In order to hydrate reservoir layers 15 and 16, as well as any optional membrane and/or adhesive layers, the liquid 20 contained in pouches 21 and 22 must be released and directed to flow into the non-hydrated portions of electrode assemblies 8 and 9, respectively. The liquid 20 in pouch 21 is released by grasping and pulling pull tab 27 in the direction of the arrow shown in FIG. 1. Pulling tab 27 causes sheet 25 to tear, thereby releasing liquid 20 into wicking layer 17. The liquid 20 is quickly absorbed by layer 17 and wicked across the entire top surface of electrode 11. Similarly, in order to hydrate the non-hydrated matrix of reservoir layer 16, liquid 20 is released from pouch 22 by grasping and pulling tab 28 in the direction of the arrows shown in FIGS. 1 and 3. Pulling tab 28 causes sheet 26 to tear, thereby releasing liquid 20 into wicking layer 18. The liquid 20 is quickly absorbed by layer 18 and wicked across the entire top surface of electrode 12. The optional wicking layers 17 and 18 may be comprised of liquid-wicking materials such as cotton, sponges, cellulose triacetate, rayon, polyesters, hydrophilic polymer resins, etc. and blends thereof. Also suitable as wicking materials are hydrophobic resin fibers, such as polypropylene or polyester fibers which have preferably been treated to produce a hydrophilic surface, thus allowing water to adsorb to the collection of fibers and be transported by capillary action with little or no water absorbed into the fibers themselves. Examples of hydrophobic polyester fibers treated to produce a wettable surface, are Coolmax® and Thermax®, both sold by E. I. DuPont de Nemours and Company of Wilmington, Del. Coolmax® and Thermax® fibers, as well as wettable polypropylene fibers and other surface-wettable hydrophobic fibers, are extremely efficient wicking fibers, transporting water along the surface of the fibers and in the spaces between fibers without retaining much water within the fibers themselves.

As an alternative to wicking layers 17 and 18, the top surface of electrodes 11 and 12 may be provided with a plurality of liquid conveying grooves particularly in cases where electrodes 11 and 12 are composed of a solid polymer matrix containing a hydrophilic water-conveying additive.

As an alternative to the plurality of liquid conveying grooves, the top surface of electrodes 11 and 12 can also be textured in substantially any known manner in order to form a plurality of small peaks and valleys of substantially any geometric configuration (e.g., a roughened surface). These small valleys convey water across the entire surface of electrodes 11 and 12.

Electrodes 11 and 12 each have a structure and/or a composition which allows the liquid 20 to pass therethrough and into the non-hydrated reservoirs 15 and 16, respectively, as well as into any optional membrane and/or adhesive layers present, and thereby hydrate and activate the electrode assemblies 8 and 9, respectively. Electrodes 11 and 12 each have at least one liquid conveying pathway therethrough to allow liquid 20 released from pouches 21 and 22, respectively, to flow into the non-hydrated matrices of reservoirs 15 and 16. For example, electrodes 11 and 12 can be formed of metal in the form of a plate (not shown) having one or more liquid conveying holes therethrough. Alternatively, electrodes 11 and 12 can be formed of a metal screen (not shown). Most preferably however, electrodes 11 and 12 are in the form of a solid polymer matrix containing both an electrically conductive filler (e.g., carbon fibers or metal powders) and a liquid conveying additive, most preferably a hydrophilic water conveying additive.

The agent (ie, a drug and/or an electrolyte salt) may be present in the non-hydrated reservoirs 15 and 16 before hydration or may be added to the non-hydrated reservoirs 15 and 16 with the liquid 20 at the time of hydration, however in the case of an agent in the form of a drug which is unstable in the presence of the hydrating liquid 20, the drug is preferably present in the non-hydrated reservoir 15 before hydration. When the non-hydrated reservoir 15 already contains the agent to be delivered, the liquid 20 preferably comprises deionized water. When the non-hydrated reservoirs 15 and 16 initially contain no agent, the liquid 20 preferably comprises an aqueous solution or suspension of a drug or an electrolyte salt. Most preferably, reservoirs 15 and 16 are each comprised of a hydrophilic polymer.

In most cases, the liquid 20 contained in pouches 21 and 22 will be composed at least in part of water. However, it is well within the scope of the present invention to "hydrate" the reservoirs 15 and 16 using other liquids including non-aqueous liquids such as alcohols and glycols. Accordingly, as used herein, the term "hydrate" refers to the release of either an aqueous or non-aqueous based liquid 20 from pouches 21 and 22. Furthermore, in those instances where the non-hydrated reservoirs 15 and/or 16 initially contain no drug or electrolyte, the hydrating liquid 20 may comprise a liquid solution or suspension of the drug or electrolyte. Liquid 20 may also contain other additives such as preservatives, agents which inhibit microbial growth, and agents which enhance the transdermal flux of drug through the skin, e.g., one or more surfactants, and combinations of these agents. In the typical case where the liquid is comprised of water, the matrix of reservoirs 15 and 16 will be at least partly composed of a hydrophilic material such as a hydrophilic polymer, a cellulosic sponge or pad, or other water retaining material. Most preferably, the reservoirs 15 and 15 are comprised of a hydrophilic polymer of the type described hereinafter.

In accordance with the present invention, at least one of electrode assemblies 8 and 9, and preferably both electrode assemblies 8 and 9, are initially in a substantially dry state. Thus, the various ion transporting layers making up electrode assemblies 8 and 9 are initially in a non-hydrated condition. As used herein, the terms "dry state" and "non-hydrated" mean that the particular layer contains an insufficient amount of liquid to permit ion transport therethrough. For example, the ion transmitting layers of donor electrode assembly 8 include reservoir 15 and any optional adhesive and/or membrane layers. Depending upon its composition, electrode 11 may also be ion-conducting. For example, if electrode 11 is a metal foil, then it is electrically conductive (ie, electron conducting) but not ion-conducting. However, if electrode 11 is composed of a hydrophilic polymer matrix (e.g., polyvinylpyrrolidone) loaded with metal particles, then electrode 11 is also ion-conducting. In order for donor electrode assembly 8 to be considered a "dry state" electrode assembly, reservoir 15 and other ion-conducting layer(s) within electrode assembly 8 initially contain an insufficient amount of liquid to allow efficient ion transport therethrough. Similarly, in order for counter electrode assembly 9 to be considered a "dry state" electrode assembly, reservoir 16 and other ion-conducting layer(s) within electrode assembly 9 initially contain an insufficient amount of liquid to allow efficient ion transport therethrough. In order to be considered "non-hydrated," reservoir layers 15 and 16 should initially contain less than about 10 wt % liquid, preferably less than about 5 wt % liquid and most preferably less than about 1 wt % liquid.

Figure 5:
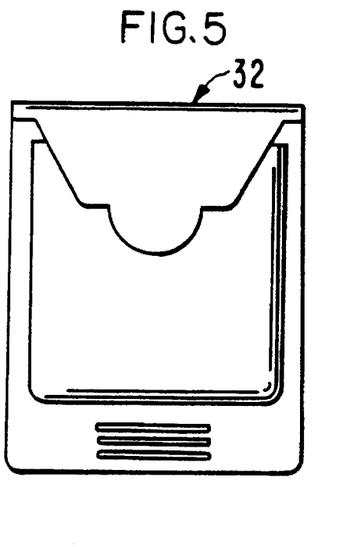
FIG. 5 is a front view of the package shown in FIG. 4.
Figure 6:
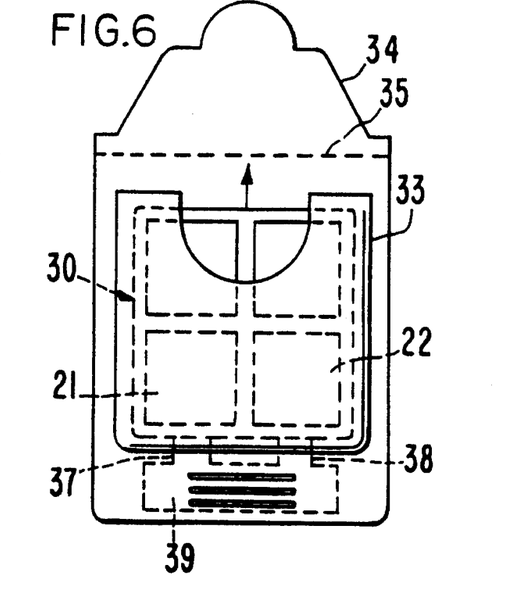
FIG. 6 is a front view of the container shown in FIGS. 4 and 5, with the iontophoretic delivery device shown in phantom.
Figures 7, 8:
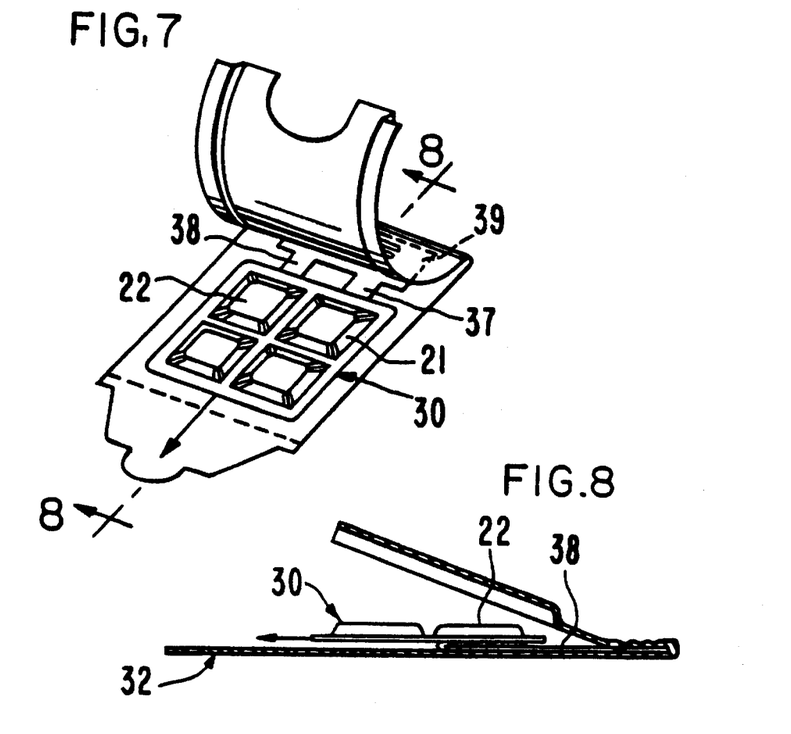
FIG. 7 is a perspective view of the package and iontophoretic delivery device shown in FIGS. 4, 5 and 6, with portions of the package opened for purposes of illustration.
FIG. 8 is a sectional view of the package and the iontophoretic delivery device shown in FIG. 7, taken along line 8—8 in FIG. 7.

In FIGS. 4–8, there is shown an alternate embodiment of an iontophoretic agent delivery device, designated by the numeral 30, according to the present invention. Device 30 is held in a package 32. Pull tabs 37 and 38 are attached to sheets 25 and 26, (not shown in FIGS. 4–8), respectively, in a similar manner to that shown in device 10 illustrated in FIG. 1. Sheets 25 and 26 are made of a material which is capable of being ripped or torn. Pull tabs 37 and 38 (FIGS. 4–8) differ from pull tabs 27 and 28 (FIGS. 1–3) in the following respect. Pull tabs 27 and 28 each have an end portion which is adapted to be grasped and pulled (relative to device 10) by the user. However, in device 30, the pull tabs 37 and 38 are not adapted to be grasped and pulled. Instead, tabs 37 and 38 are attached to the package 32. As best shown in FIGS. 6 and 7, the individual tabs 37 and 38 terminate in an integral tab member 39. Tab member 39 is attached (e.g., by gluing, heat sealing or by mechanical attachment, e.g., stapling) to the package 32. As best shown in FIGS. 5 and 6, package 32 has a pocket 33 within which device 30 sits. Pocket 33 can be opened by unfolding closure member 34 along fold line 35. Device 30 is removed from pocket 33 by grasping device 30 and pulling in the direction of the arrows shown in FIGS. 6, 7 and 8. Because tab member 39 is attached to the package 32, removal of device 30 from pocket 33 automatically causes tabs 37 and 38 to be pulled relative to device 30, thereby ripping or tearing the liquid impermeable sheets 25 and 26 which seal the pouches 21 and 22, respectively. Thus, the dry state electrode assemblies of device 30 are automatically hydrated by the action of removing device 30 from package 32.

Figure 9:
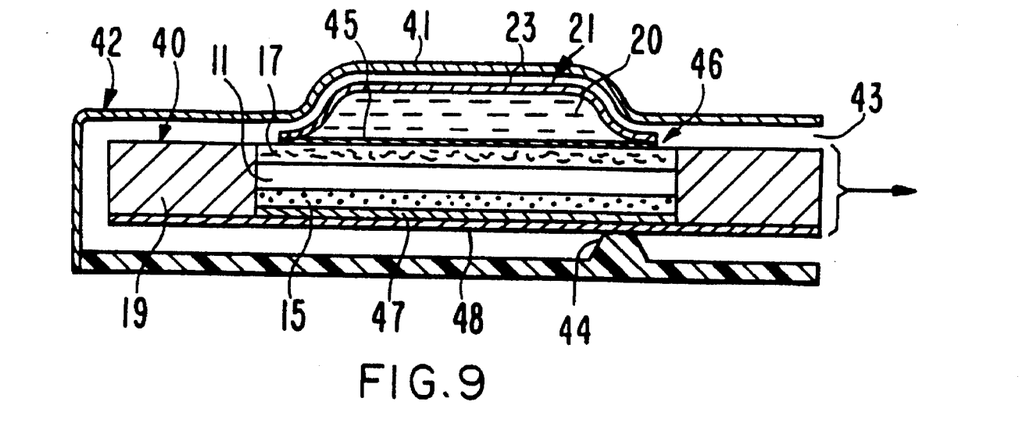
FIG. 9 is a side sectional view of an iontophoretic delivery device and a package therefor in accordance with another embodiment of the present invention.

In FIG. 9, there is illustrated another embodiment of an iontophoretic agent delivery device, designated by the numeral 40, according to the present invention. Like the device 30 illustrated in FIGS. 4–8, device 40 is also automatically hydrated upon removal from package 42. Device 40, has a liquid containing pouch 21 having a flexible wall 23. For example, flexible wall 23 may be comprised of any liquid-impermeable, formable and flexible film or foil material and preferably is formed of polyethylene or polypropylene film, or soft formable aluminum foil. Pouch 21 is sealed along the side adjacent wicking layer 17 with a liquid impermeable material 45 shown in the form of a sheet. Sheet 45 is designed to rupture when the pressure within sealed container 21 reaches a predetermined level. For example, sheet 45 may be formed of a metal foil and is preferably formed of brittle aluminum foil, most preferably brittle aluminum foil which has been treated on its interior surface with a material which resists water induced degradation of the foil and/or which can be neat sealed with the material of wall 23.

Package 42 is composed of a relatively rigid material such as cardboard, paperboard, rigid plastics or the like. The top wall of package 42 optionally has a raised portion 41 which closely accommodates the shape of pouch 21. Alternatively, a protuberance 44 which extends into the interior of package 42 may be provided. Package 42 has a compression zone 46 formed by either (1) the necked-down part of portion 21 in combination with the bottom of package 42, (2) the top of package 42 and the protuberance 44, or (3) a combination of (1) and (2) above. Those skilled in the art will readily appreciated that portion 41 and protuberance 44, either alone or in combination, may be used to form compression zone 46. Many additional configurations to package 42 for forming compression zone 46 will be obvious in light of the teachings herein. During storage of device 40 within package 42, pouch 21 is located outside of the compression zone 46. The compression zone 46 is located between the "stored" position of pouch 21 within package 42 and the opening 43 to package 42.

In order to activate device 40, device 40 is slid out of package 42 in the direction of the arrow, forcing pouch 21 into the compression zone 46. When pouch 21 encounters compression zone 46, the pouch is squeezed thereby increasing the pressure within pouch 21 to a level at least as great as the predetermined level, thereby causing sheet 45 to rupture. Once ruptured, the liquid 20 within pouch 21 is released into the optional wicking layer 17 and through electrode 11 into the non-hydrated matrix of reservoir 15 similar to device 10. In addition to the dry agent reservoir 15, device 40 also includes a non-hydrated layer 47 of an ion-conducting adhesive. A release liner 48 is provided on the bottom surface of device 40 and is adapted to be removed prior to placement of device 40 on the body surface.

Figure 10:
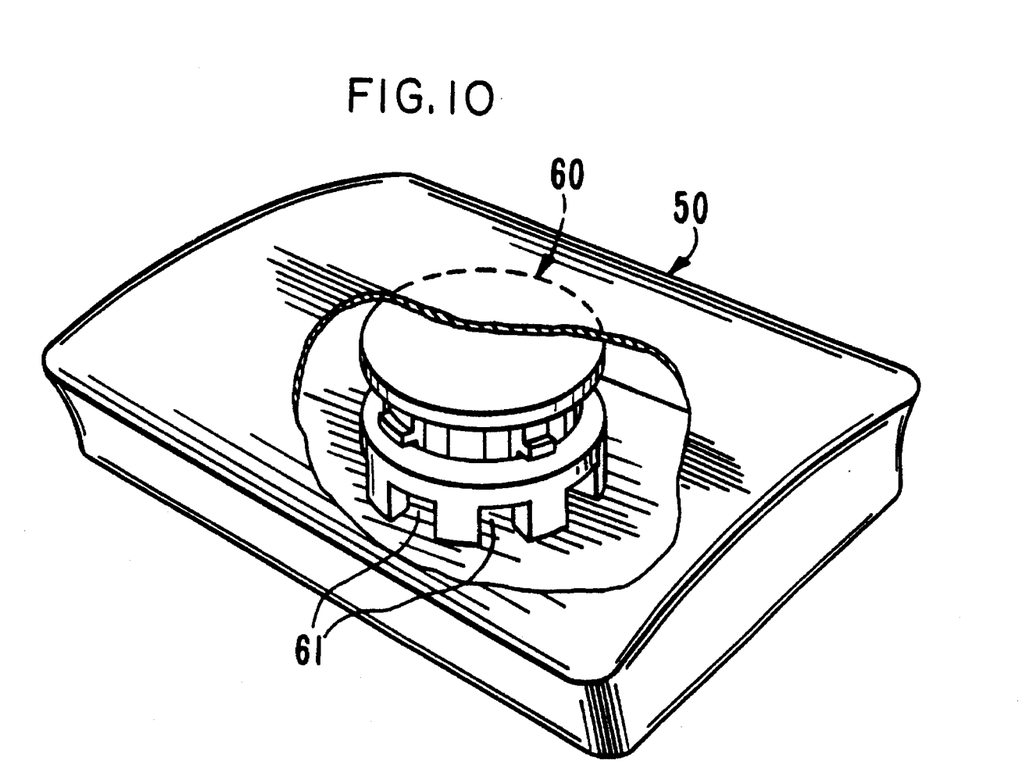
FIG. 10 is a perspective view of a fluid reservoir container, with parts shown in phantom, useful for hydrating an iontophoretic delivery device in accordance with another embodiment of the present invention.
Figure 11:
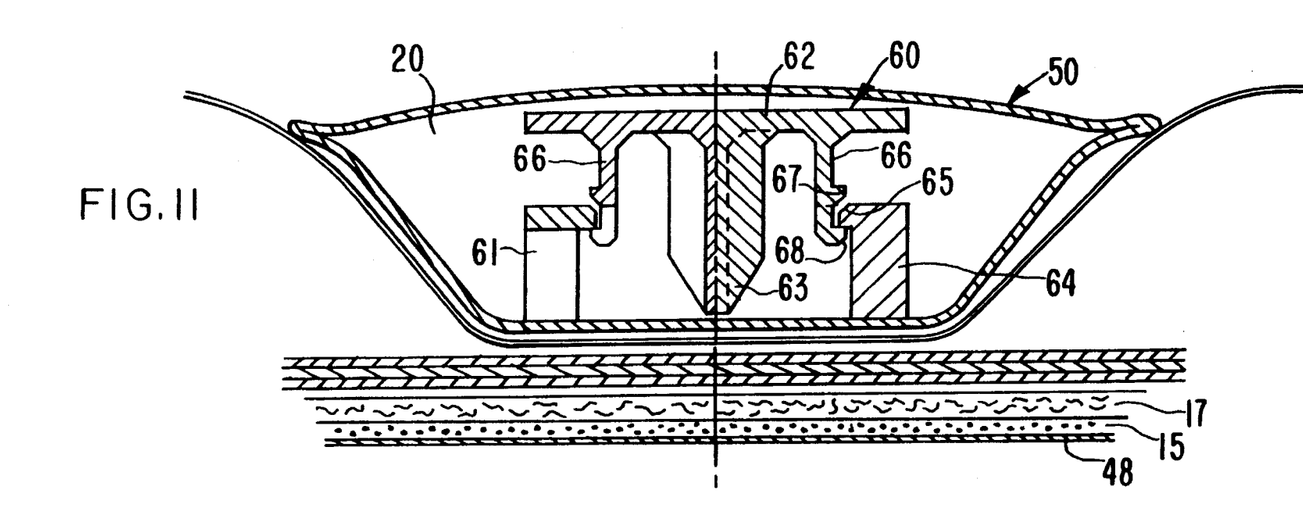
FIG. 11 is a side sectional view of the fluid reservoir container shown in FIG. 10, with a punch in an up or ready position, ie, before hydration of the underlying electrode assembly.
Figure 12:
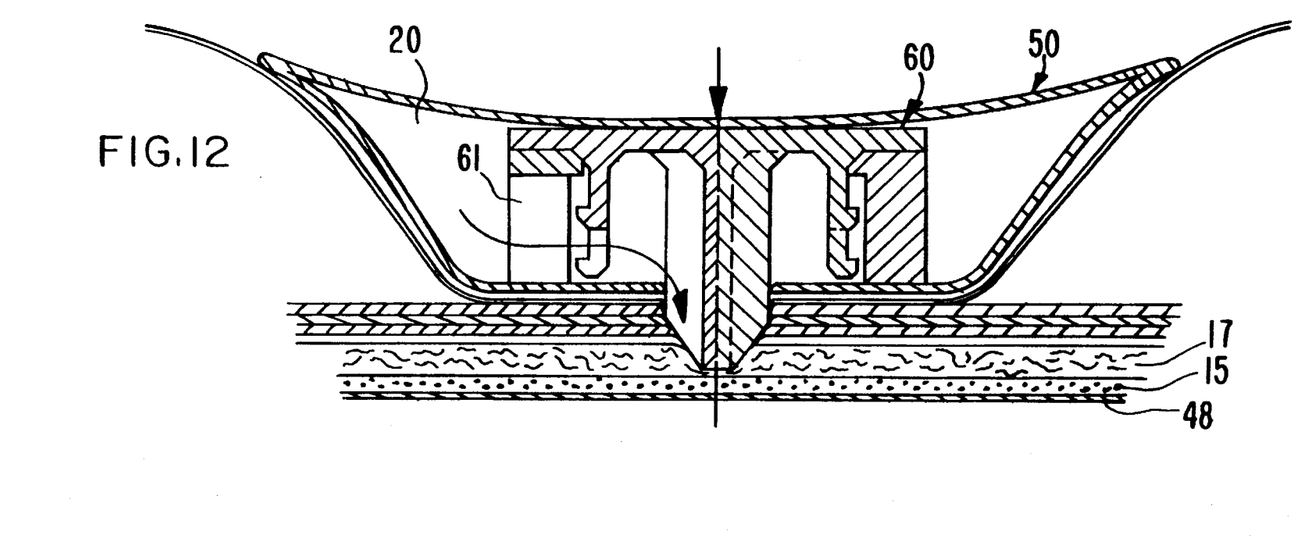
FIG. 12 is another side sectional view of the fluid reservoir container shown in FIGS. 10 and 11 with the punch in a down or activated position for hydration of the underlying electrode assembly.

In FIGS. 10–12, there is illustrated another embodiment of a liquid-containing container in the form of a pouch used for hydrating a non-hydrated reservoir matrix in an iontophoretic delivery device. In FIG. 10, there is illustrated a sealed pouch 50 which contains a hydrating liquid 20. The wall of pouch 50 is formed of flexible sheet material such as polyethylene, polypropylene or a polyester/foil laminate such as Medpar® sold by the Minnesota Mining and Manufacturing Co. of St. Paul, Minn. Positioned within pouch 50 is a punch 60. In FIGS. 10 and 11, punch 60 is in the up or ready position whereas in FIG. 12, punch 60 is shown in the down or activated position. Alternatively, two or more punches 60 may be positioned within pouch 50.

Referring now to FIG. 11, punch 60 is comprised of a plunger 62 and a stand 64. Plunger 62 has a blade 63 with a "+" shaped cross-section. Surrounding blade 63 are a plurality of spaced prongs 66, each prong 66 having a pair of spaced raised ridges 67 and 68. Stand 64 has an annular shape with slots 61 which permit liquid 20 to flow into the hole created by blade 63, as shown by the fluid flow arrow in FIG. 12. Stand 64 also has an inwardly projecting lip 65. Lip 65 is shaped to engage prongs 66 with the lip 65 positioned between ridges 67 and 68 as shown in FIG. 11. Blade 63 may be made of any rigid material having sufficient strength to puncture the wall of pouch 50 when the top of pouch 50 is compressed as shown by the arrow in FIG. 12.

Preferably, punch 60 is composed of a rigid polymer material such as polycarbonate, polysulfone or rigid polyvinyl chloride. As plunger 62 is pushed into stand 64, ridge 67 is squeezed past lip 65. Eventually blade 63 cuts through the bottom wall of pouch 50, and penetrates through various upper layers in the iontophoretic delivery device with the point of blade 63 ending within wicking material 17 as best shown in FIG. 12. Liquid within pouch 50 flows through slots 61 and along the open areas of the "+" shaped cross-section of blade 63 and into optional wicking layer 17, which wicks the liquid across the upper surface of non-hydrated reservoir 15.

A dry state iontophoretic delivery device having one or more liquid-containing pouches 50 may be used in conjunction with a package of the type illustrated in FIG. 9 and having a compression zone 46. The device can be held in the package with the pouch(es) 50 located outside compression zone 46. When the device is removed from the package, the pouch 50 is forced through compression zone 46 causing flexible pouch 50 to be compressed, thereby activating punch 60 by pushing plunger 62 into stand 64.

Alternatively, punch 60 can be activated by having the user press on the top of pouch 50 using ordinary finger pressure.

The lip 65 in conjunction with the spaced ridges 67 and 68 provide an important advantage not found in prior art hydratable devices. With devices such as those disclosed in Konno et al U.S. Pat. No. 4,842,577, there was a tendency for the seal between the water reservoir and the non-hydrated portions of the electrode to be inadvertently broken during manufacture, packaging and/or handling of the electrode. With the present design, this problem has been eliminated since slight pressures exerted on pouch 50 which have a tendency to push plunger 62 into stand 64 are insufficient to overcome the resistance provided by the interaction between the lip 65 and the ridge 67 thereby preventing inadvertent hydration of the underlying electrode assembly caused by pressure inadvertently applied to pouch 50. Thus, the present design provides an important improvement over that disclosed by Konno et al.

Figure 13:
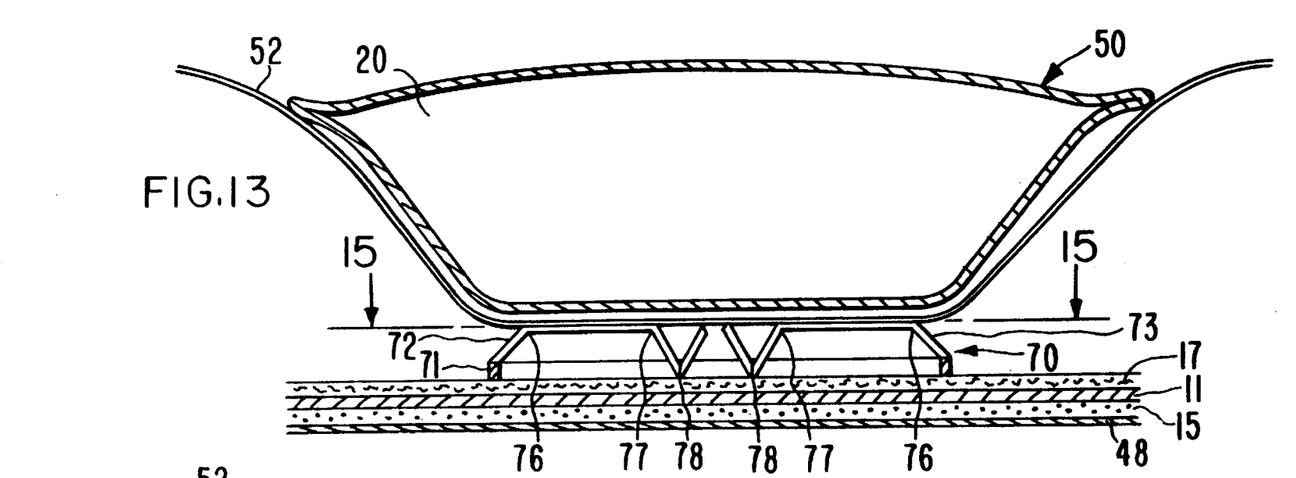
FIG. 13 is a side sectional view of a fluid reservoir container and portions of an iontophoretic delivery device, with an alternative punch in a ready position, ie, before hydration of the underlying electrode assembly.
Figure 14:
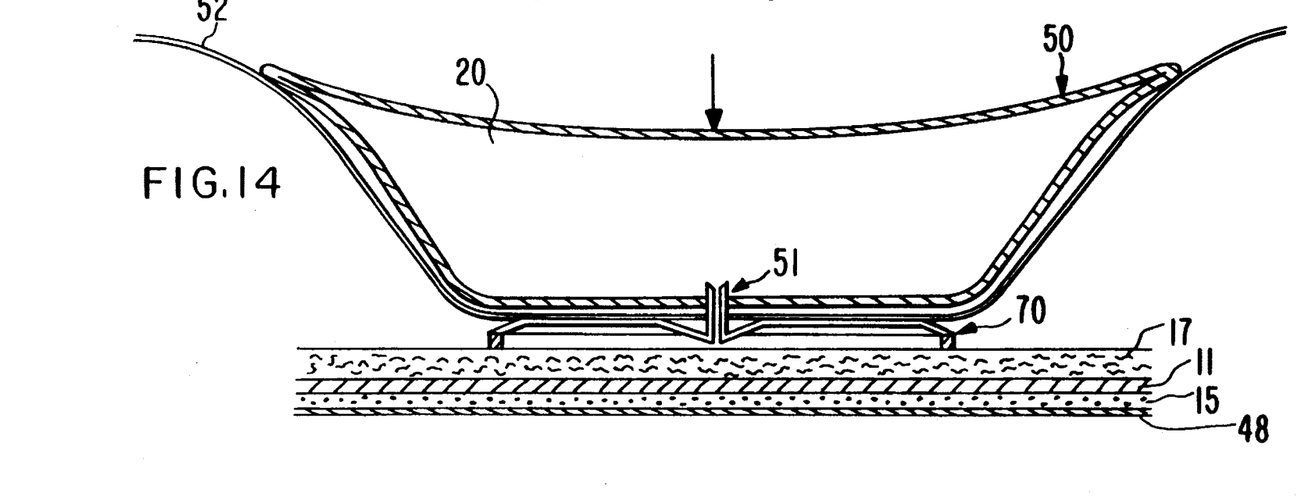
FIG. 14 is another side sectional view of the fluid reservoir container and iontophoretic delivery device shown in FIG. 13, with the punch in an activated position for hydration of the underlying electrode assembly.
Figure 15:
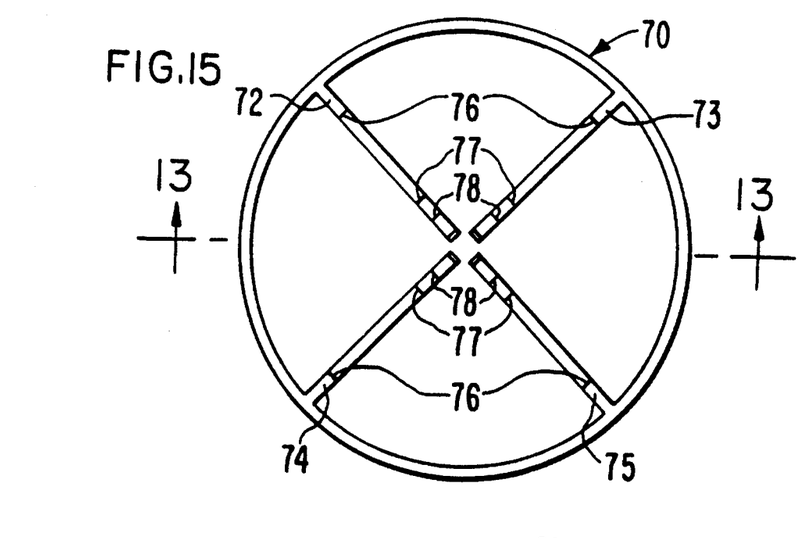
FIG. 15 is a top view of the punch illustrated in FIGS. 13 and 14.

In FIGS. 13–14, there is illustrated another embodiment of a liquid-containing container in the form of a pouch used for hydrating a non-hydrated reservoir matrix in an iontophoretic delivery device. In FIG. 13, there is illustrated a sealed pouch 50 which contains a hydrating liquid 20. The wall of pouch 50 is formed of flexible sheet material such as polyethylene, polypropylene, or a polyester/foil laminate such as Medpar®. Positioned underneath pouch 50 is a punch 70. In FIG. 13, punch 70 is in a ready position whereas in FIG. 14, punch 70 is shown in an activated position. A top view of punch 70 is shown in FIG. 15 whereas the view of punch 70 illustrated in FIG. 13 is taken along lines XIII—XIII in FIG. 15. Punch 70 is comprised of a ring-shaped member 71 having a plurality (e.g., four) biased blades 72, 73, 74 and 75, each of which extends radially inwardly from member 71. The member 71 and the blades 72, 73, 74 and 75 may be formed of a single integral member, or alternatively, the blades 72, 73, 74 and 75 can be separately formed and then later attached by appropriate means to member 71. For example, member 71, and blades 72, 73, 74 and 75 may be formed of metal and the blades may be attached, e.g. by welding, to member 71. Alternatively, punch 70 may be formed by a metal stamping operation. Still alternatively, the member 71 and the blades 72, 73, 74 and 75 can be a single integral piece formed e.g., by molding an appropriate polymer such as an ABS copolymer, a polyamide, or nylon.

As best shown in FIG. 13, each of the blades 72–75 has a plurality of bends 76–78 therein. Bend 78 is substantially less flexible than bends 76 and 77 and accordingly, bends 78 do not straighten out when downward pressure is applied to the top of blades 72–75. Further, each of the blades has a free end which is oriented generally in a direction pointing towards the bottom of pouch 50. When pressure is applied to the top of pouch 50 as shown by the arrow in FIG. 14, the pouch 50 is forced downwardly against blades 72, 73, 74 and 75. This downward pressure causes the more flexible bends 76 and 77 in blades 72 and 73 to straighten, forcing the blades 72–75 is into the configuration shown in FIG. 14. As will be readily appreciated, the natural bias of the blades 72–75 causes their free ends (which are preferably sharpened to enhance their ability to puncture through backing layer 52 and pouch 50) to extend upwardly eventually puncturing backing layer 52 and the bottom wall of pouch 50, forming a hole 51 therethrough. Once hole 51 is formed, liquid 20 within pouch 50 flows out of the pouch 50, through hole 51, through the open base of ring-shaped member 71, and into the wicking layer 17. The hydrating liquid 20 flows through the electrode layer 11 and into the non-hydrated agent reservoir 15.

A dry state iontophoretic delivery device having a liqui-containing pouch 50 and a punch 70 may be used in conjunction with a package of the type illustrated in FIG. 9 and having a compression zone 46. The device can be held in the package with the pouch located outside compression zone 46. When the device is removed from the package, the pouch 50 is forced through compression zone 46 causing flexible pouch 50 to be compressed, thereby activating punch 70 by forcing blades 72–75 to puncture the underside of pouch 50. Alternatively, punch 70 can be activated by having the user press on the top of pouch 50 using ordinary finger pressure prior to using the device.

Figures 16, 17:
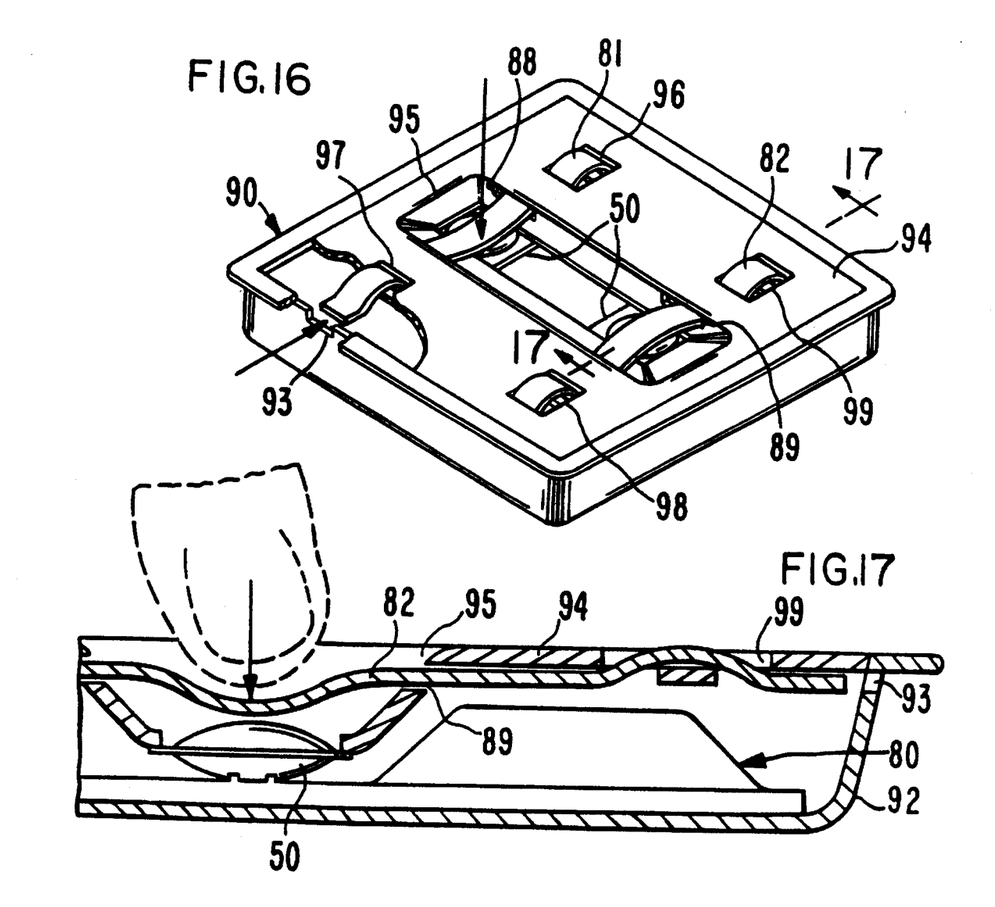
FIG. 16 is a perspective view of a package for an iontophoretic delivery device, with means for automatically hydrating the device upon opening of the package.
FIG. 17 is a side sectional view of the package and the device shown in FIG. 16, taken along line 17—17.

In FIGS. 16 and 17 there is shown another iontophoretic delivery device 80 which is automatically hydrated upon removal from its package 90. Package 90 is comprised of a tray 92 and a lid 94. Lid 94 is provided with openings 95–99. The tray 92 is provided with four slots 93. Two strips 81 and 82 are provided in lid 94 as shown in FIG. 16. Strip 81 has two ends, each of which engages a slot 93. Similarly, strip 82 has two ends, each of which engages other slots 93 in tray 92 (not shown in FIG. 16). Strip 81 is threaded through openings 96 and 97 and passes across opening 95 above pouch 50 by way of slots 88. Similarly, strip 82 is threaded through openings 98 and 99 and passes across opening 95 above a second pouch 50 by way of slots 89.

In a stored condition, the ends of strips 81 and 82 extend into slots 93, thereby securing lid 94 within tray 92.

In order to remove lid 94, the strips 81 and 82 must be depressed in the region of opening 95 as best shown in FIG. 17. Depression of strips 81 and 82 causes the strips to withdraw from at least two of the slots 93 located on the same side of tray 92, and preferably causes the strips to withdraw from all four slots 93 on both sides of tray 92, as best shown by the arrow in FIG. 16. In addition, depression of strips 81 and 82 in the region of opening 95 causes pressure to be exerted on pouches 50, which causes pouches 50 to break and release water to the non-hydrated portions of device 80 in a manner consistent with that disclosed earlier herein. As will be appreciated by those skilled in the art, package 90 provides a means for automatically hydrating device 80 upon removal of device 80 from package 90.

Figure 18:
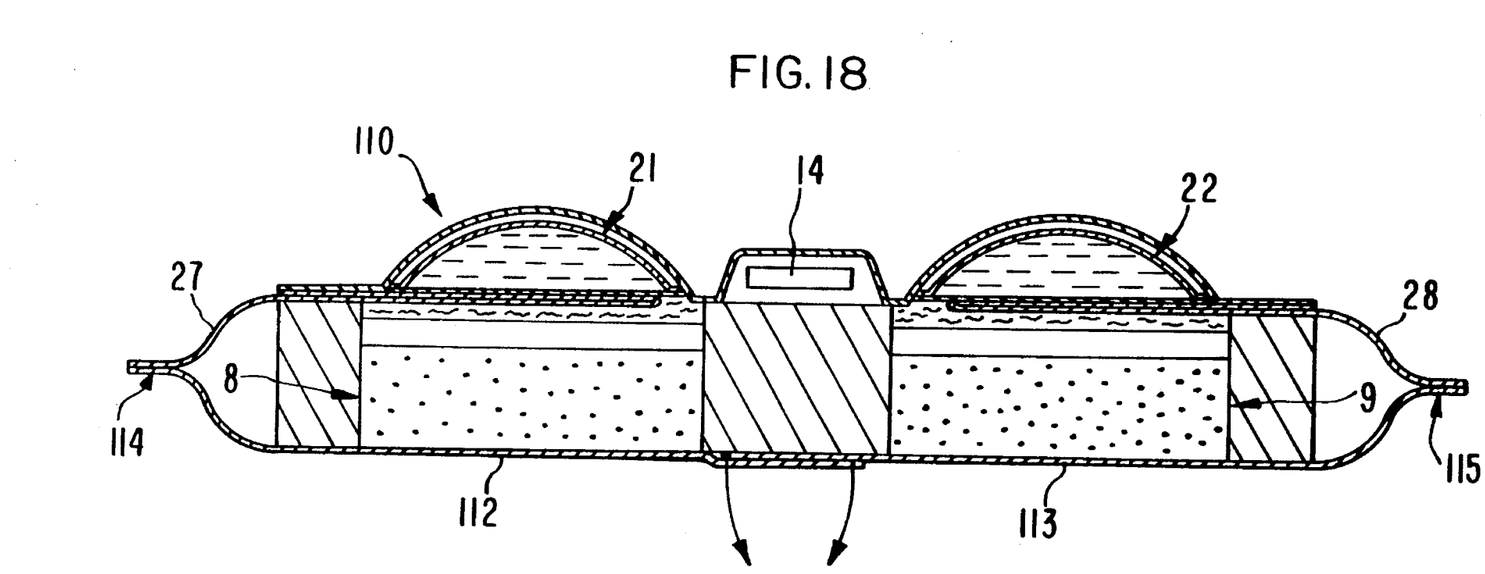
FIG. 18 is a side sectional view of another iontophoretic drug delivery device according to the present invention.

In FIG. 18 there is shown another iontophoretic delivery device 110. Device 110, like device 10 shown in FIG. 1, includes a non-hydrated donor electrode assembly 8 and a non-hydrated counter electrode assembly 9. Covering the skin contacting surfaces of donor electrode assembly 8 and counter electrode assembly 9 are release liners 112 and 113, respectively. Release liners 112 and 113 are typically comprised of a siliconized polyester material. One end of release liner 112 is fixedly attached to tab 27. Release liner 112 and tab 27 are attached to one another using conventional means (not shown) such as gluing, stapling, etc, in the region designated 114. Similarly, release liner 113 is attached to tab 28 in the region 115 using conventional attachment means. Before use, the patient or physician peels the release liners 112,113 off the surfaces of electrode assemblies 8 and 9, respectively, as shown by the arrows. Once the release liners 112 and 113 are peeled away from the skin contacting surfaces of the electrode assemblies 8 and 9, the patient or physician further pulls the release liners outwardly from device 110, causing tabs 27 and 28 to be pulled relative to pouches 21 and 22, respectively. This pulling action operates to both open the water containing pouches 21 and 22 in a similar manner to that described in connection with device 10 shown in FIG. 1 and also removes the release liners 112 and 113. This configuration assures that the electrode assemblies 8 and 9 are hydrated, and thus device 110 is activated, prior to placement on the body since the release liners 112 and 113 must first be removed before the device 110 can be secured in place on the body surface.

When used in connection with the reservoir 15 or the donor electrode assembly 8, the term "agent" refers to beneficial agents, and preferably to beneficial agents such as drugs, within the class which can be delivered through body surfaces such as skin and mucosal membranes. Most preferably, the beneficial agent is soluble in the liquid used to "hydrate" the donor electrode assembly 8.

The expression "drug" is intended to have a broad interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, psychostimulants, sedatives and tranquilizers.

The invention is particularly useful in the controlled delivery of peptides, polypeptides, proteins, macromolecules and other drugs which have a tendency to be unstable, hydrolyzed, oxidized, denatured or otherwise degraded in the presence of the liquid, such as water, necessary to conduct iontophoresis. For example, drugs containing either an ester bond (ie, steroids) or an amide bond (ie, peptides) may be hydrolyzed in water. Specific examples of drugs which can become degraded in the presence of water include catachols, such as apomorphine and epinephrine, salbutamol, sulfhydryls such as captopril, niphedipine, and peptides such as VIP and insulin.

Examples of other peptides and proteins which may be delivered using the device of the present invention include, without limitation, LHRH, LHRH analogs such as buserelin, gonadorelin, naphrelin and leuprolide, GHRH, insulin, heparin, calcitonin, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc.), follicle luteolds, αANF, growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hyaluronidase, interferon, interteukin-2, menotropins (urofollitropin (FSH) and LH), oxytocin, streptokinase, tissue plasminogen activator, urokinase, vasopressin, ACTH analogs, ANP, ANP clearance inhibitors. angiotensin II antagonists. antidiuretic hormone agonists, antidiuretic hormone antagonists, bradykinin antagonists, CD4, ceredase, CSF's, enkephalins. FAB fragments, IgE peptide suppressors, IGF-1, neurotrophic factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 anti-trypsin (recombinant).

When used in connection with the reservoir layer 16 and/or the counter electrode assembly 9, the term "agent" refers to any suitable pharmacologically acceptable electrolyte salt. Preferably, the electrolyte salt is soluble in the liquid used to "hydrate" the counter electrode assembly 9. Suitable electrolyte salts include water soluble and biocompatible salts such as sodium chloride, alkali metal salts, alkaline earth metal salts such as chlorides, sulfates, nitrates, carbonates, phosphates, and organic salts such as ascorbates, citrates, acetates and mixtures thereof.

Electrodes 11 and 12 are electrically conductive and may be formed of a metal, or other electrically conductive material. For example, electrodes 11 and 12 may be formed of a metal foil, a metal screen or metal deposited or painted on a suitable backing. Examples of suitable metals include silver, zinc, silver/silver chloride, aluminum, platinum, stainless steel, gold and titanium. Alternatively, the electrodes 11 and 12 may be formed of a polymer s matrix containing a conductive filler such as a metal powder, powdered graphite, carbon fibers or other known electrically conductive filler material. The polymer based electrodes may be made by mixing the conductive filler in a preferably hydrophobic polymer matrix. For example, zinc powder, silver powder, silver/silver chloride powder, powdered carbon, carbon fibers and mixtures thereof can be mixed in a hydrophobic polymer (e.g., an ethylene vinyl acetate copolymer) matrix, with the preferred amount of conductive filler being within the range of about 30 to 90 vol % and the remainder being the hydrophobic polymer matrix.

When the electrodes 11 and 12 are positioned between the liquid containing pouches 21, 22 and the non-hydrated reservoirs 15, 16, respectively, the electrodes 11 and 12 should also be able so transmit the hydrating liquid released from pouches 21 and 22, into the non-hydrated reservoirs 15 and 16, respectively. This can be accomplished by forming one or more liquid conducting pathways through the otherwise solid electrodes 11 and 12. Alternatively, the electrodes 11 and 12 can be in the form of a metal screen. If the electrodes are formed of a hydrophobic polymer matrix containing a conductive filler, the matrix can be made water permeable by adding a suitable amount (e.g., 10 to 40 vol %) of a hydrophilic additive. Preferred hydrophilic additives include the hydrophilic polymers used in the matrices of reservoirs 15 and 16.

In the devices illustrated in the figures, the liquid containing pouches 21 and 22 have been positioned on the top surfaces of the devices. In this position, the liquid released from the is pouches 21, 22 must be controlled to flow through the electrode layers 11 and 12, respectively. Thus, in the devices illustrated in the figures, the liquid flow control means have been shown in the form of "flow through" electrodes which are permeable to the hydrating liquid 20, optionally with a layer 17, 18 of a wicking material which evenly distributes the flow of liquid 20 across the top surfaces of electrodes 11 and 12, respectively. However, it is well within the scope of the present invention to position the liquid containing pouches 21 and 22 in other locations, for example at the side edges of the delivery devices in which case either or both of (1) the "flow through" characteristics of electrodes 11 and 12 and (2) the wicking layers 17 and 18 may be unnecessary. Those skilled in the art may appreciate that the term "liquid flow control means" is used herein to broadly define any means for controlling the flow of liquid released from pouches 21 and 22 into the non-hydrated portions of the device and is not limited specifically to the "flow through" electrodes and the wicking materials illustrated in the figures.

Electrodes 11 and 12 are electrically connected to the power source in layer 14 using well known means, e.g., printed flexible circuits, metal foils, wires or by direct contact. As an alternative to a battery as the power source, device 10 can be powered by a galvanic couple formed by the donor electrode 11 and counter electrode 12 being composed of dissimilar electrochemical couples and being placed in electrical contact with one other. Typical galvanic couple materials for delivering a cationic agent include a zinc donor electrode 11 and a silver/silver chloride counter electrode 12. A Zn-Ag/AgCl galvanic couple provides an electrical potential of about 1 volt.

The matrix of reservoirs 15 and 16 can be any material adapted to absorb and hold a sufficient quantity of liquid therein in order to permit transport of agent therethrough by iontophoresis. For example, gauzes made of cotton or other absorbent fabrics as well as pads and sponges, both natural and synthetic, may be used. More preferably, the matrix of reservoirs 15 and 16 is composed, at least in part, of a hydrophilic polymer material. Most preferably, the matrix of reservoirs 15 and 16 is a solid polymer matrix composed at least in part of a hydrophilic polymer. Both natural and synthetic hydrophilic polymers may be used. Suitable hydrophilic polymers include copolyesters such as Hytrel® sold by DuPont de Nemours & Co. of Wilmington, Del., polyvinylpyrrolidones, polyvinyl alcohol, polyethylene oxides such as Polyox® manufactured by Union Carbide Corp., Carbopol® manufactured by BF Goodrich of Akron, Ohio; blends of polyoxyethylene or polyethylene glycols with polyacrylic acid such as Polyox® blended with Carbopol®, polyacrylamide, Klucel®, cross-linked dextran such as Sephadex (Pharmacia Fine Chemicals, AB, Uppsala, Sweden), Water Lock® (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-Di-Sol (FMC Corp., Philadelphia, Pa.), hydrogels such as polyhydroxyethyl methacrylate (National Patent Development Corp.), natural gums, chitosan, pectin, starch, guar gum, locust bean gum, and the like, along with blends thereof. Of these, polyvinylpyrrolidones are preferred.

Optionally, the matrix of reservoirs 15 and 16 may also contain a hydrophobic, preferably heat fusible, polymer in order to enhance the lamination of reservoir layers 15 and 16 to the adjacent layers (e.g., insulators 26 and 27, electrodes 11 and 12 and any optional membrane and/or adhesive layers). Suitable hydrophobic polymers for use in the matrix of reservoir layers 15 and 16 include, without limitation, polyethylene, polypropylene, polyisoprenes and polyalkenes, rubbers, copolymers such as Kraton®, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, n-pentanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, and itaconic acid, N-branched alkyl maleamic acids wherein the alkyl group has 10–24 carbon atoms, glycol diacrylates, and blends thereof. Most of the above listed hydrophobic polymers are heat fusible. Of these, ethylene vinyl acetate copolymers are preferred.

When the drug or electrolyte is present in the reservoir matrix before hydration, blending of the drug or electrolyte with the hydrophilic polymer matrix components can be accomplished mechanically, either by milling, extrusion or hot melt mixing, for example. The resulting reservoir layers may then be prepared by solvent casting, extrusion or by melt processing, for example. In addition to the drug and electrolyte, the reservoirs 15 and 16 may also contain other conventional materials such as dyes, pigments, inert fillers, and other excipients.

The combined skin-contacting areas of electrode assemblies 8 and 9 can vary from less than 1 cm$^2$ to greater than 200 cm$^2$. The average device 10 however, will have electrode assemblies with a combined skin-contacting area within the range of about 5 to 50 cm$^2$.

Having thus generally described our invention and described in detail certain preferred embodiments thereof, it will be readily apparent that various modifications to the invention may be made by workers skilled in the art without departing from she scope of this invention and which is limited only by the following claims.

What is claimed is:

1. A packaged agent delivery device, comprising:
   (a) a reservoir including a substantially non-hydrated, hydratable polymer matrix containing the agent to be delivered, the agent being unstable in the presence of a liquid for hydrating the substantially non-hydrated matrix;
   (b) a sealed container in fluid communication with the reservoir, the container containing the liquid, at least a portion of the container comprising a liquid impermeable, breakable material;
   (c) a package which contains the delivery device before use; and
   (d) means operatively associated with the package and the liquid impermeable material whereby removal of the device from the package causes said means to break the liquid impermeable material, thereby releasing the liquid from the container and into the reservoir matrix.

2. The device of claim 1, wherein the agent comprises a drug.

3. The device of claim 1, wherein the agent comprises a drug which has a tendency to be hydrolyzed, oxidized, denatured or degraded in the presence of the liquid.

4. The device of claim 1, wherein the agent is selected from the group consisting of peptides, polypeptides, proteins and macromolecules.

5. The device of claim 1, 2, 3 or 4, wherein the liquid comprises water.

6. The device of claim 1, wherein the agent is a polypeptide selected from the group consisting of growth hormones, growth factors, somatotropins and calcitonin.

7. The device of claim 1, wherein the polymer is selected from the group consisting of polyesters, polyvinylpyrrolidones, polyvinyl alcohols, polyethylene oxides, polyethylene glycols, polyacrylic acids, polyacrylamides, dextrans and cellulosic polymers.

8. The device of claim 1, wherein the reservoir matrix is adapted to be placed in agent transmitting relation with a body surface.

9. The device of claim 1, wherein the liquid impermeable material is capable of being ripped or torn and the means operatively associated with the liquid impermeable material comprises a tab, one portion of said tab being attached to the liquid impermeable material, another portion of the tab being attached to the package.

10. The device of claim 1 or 9, wherein the liquid impermeable material has a tear strength in the range of about 0.2 to 2.3 kg.

11. The device of claim 1, wherein the liquid impermeable material is rupturable when the pressure within the container reaches a predetermined level and the means operatively associated with the rupturable material comprises a compression zone within the package, whereby removal of the device from the package causes the container to move into the compression zone and increase the pressure within the container to a level at least as great as the predetermined level.

* * * * *